(12) United States Patent  (10) Patent No.: US 7,765,880 B2
Cheng et al.  (45) Date of Patent: Aug. 3, 2010

(54) FLEXIBLE PIEZORESISTIVE INTERFACIAL SHEAR AND NORMAL FORCE SENSOR AND SENSOR ARRAY

(75) Inventors: Ching-Hsiang Cheng, Hong Kong (HK); Chen Chao, Hong Kong (HK)

(73) Assignee: Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 12/123,179

(22) Filed: May 19, 2008

(65) Prior Publication Data

US 2009/0282930 A1  Nov. 19, 2009

(51) Int. Cl.
 *G01L 1/22* (2006.01)
(52) U.S. Cl. ................................. 73/862.627
(58) Field of Classification Search ............ 73/862.621, 73/862.625, 862.627
 See application file for complete search history.

(56) References Cited

U.S. PATENT DOCUMENTS

| | | | |
|---|---|---|---|
| 4,155,265 A | | 5/1979 | Pickett et al. |
| 4,503,705 A | * | 3/1985 | Polchaninoff ................. 73/172 |
| 4,896,543 A | * | 1/1990 | Gullman ................ 73/862.041 |
| 5,209,126 A | * | 5/1993 | Grahn .................... 73/862.046 |
| 5,313,840 A | | 5/1994 | Chen et al. |
| 5,452,219 A | * | 9/1995 | Dehoff et al. ................ 700/163 |
| 5,490,427 A | | 2/1996 | Yee et al. |
| 5,571,973 A | | 11/1996 | Taylot |
| 6,071,819 A | | 6/2000 | Tai et al. |
| 6,155,120 A | | 12/2000 | Taylor |
| 6,159,761 A | * | 12/2000 | Okada .......................... 438/53 |
| RE37,065 E | | 2/2001 | Grahn |
| 6,341,532 B1 | | 1/2002 | Xu et al. |
| 6,444,487 B1 | | 9/2002 | Boggs et al. |
| 6,637,276 B2 | * | 10/2003 | Adderton et al. ......... 73/862.41 |
| 6,776,049 B2 | | 8/2004 | Johnson et al. |
| 6,823,744 B2 | | 11/2004 | Ohsato et al. |
| 6,825,539 B2 | | 11/2004 | Tai et al. |
| 6,877,385 B2 | | 4/2005 | Fang et al. |
| 6,912,914 B2 | | 7/2005 | Pfeifer et al. |
| 6,951,143 B1 | * | 10/2005 | Adderton et al. ....... 73/862.044 |
| 6,955,094 B1 | | 10/2005 | Tarler |
| 7,077,011 B2 | | 7/2006 | Johnson et al. |
| 7,227,295 B2 | * | 6/2007 | Or et al. ...................... 310/328 |
| 7,320,253 B2 | * | 1/2008 | Hanazawa et al. ..... 73/862.042 |
| 7,472,611 B2 | * | 1/2009 | Hanazawa et al. ..... 73/862.626 |
| 2005/0275502 A1 | * | 12/2005 | Goebel et al. ................. 338/42 |
| 2006/0175934 A1 | * | 8/2006 | Or et al. ..................... 310/328 |

OTHER PUBLICATIONS

Shimojo et al., "A Tactile Sensor Sheet Using Pressure Conductive Rubber With Electrical-Wires Stitched Method", IEEE Sensors Journal, vol. 4, No. 5, pp. 589-596, (2004).

* cited by examiner

*Primary Examiner*—Lisa M Caputo
*Assistant Examiner*—Freddie Kirkland, III
(74) *Attorney, Agent, or Firm*—George G. Wang; Wilkinson & Grist

(57) ABSTRACT

A force sensor includes a polymeric substrate including a cavity with a tilt plane, at least two metal piezoresistors on the tilt plane, and a contact pad connected to the metal piezoresistors. The tilt plane may include a measured interface of from 15° to 75°.

26 Claims, 5 Drawing Sheets

FLEXIBLE PIEZORESISTIVE INTERFACIAL SHEAR AND NORMAL FORCE SENSOR AND SENSOR ARRAY

BACKGROUND

Force sensors, commonly known as transducers, can convert an applied mechanical pressure, acceleration, strain, or other force into an electrical output signal. Piezoresistive sensors are force sensors that use the piezoelectric effect to measure pressure, acceleration, strain, or other force by converting the force input to an electrical output signal. Traditional force sensors are capable of measuring only the compressive force component of an applied force, and are incapable of measuring the shear force component simultaneously.

Diabetes mellitus (DM) is a prevalent disease. In Hong Kong, China, for example, approximately 15% of the population suffers from DM. Of these DM patients, about 5% of them suffer from "diabetic foot" complications. Moreover, the pressure points on the foot may cause pressure ulcers associated with diabetic foot. Shear force is a key factor that may cause pressure ulcers, in addition to the pressure generated by normal force.

Consequently, it is desirable to manufacture a force sensor that can measure both the shear force component as well as the compressive force component from an applied force. It is also desirable to manufacture a 2-D force sensor array for pressure mapping applications, for example, one that is useful in preventive and predictive diagnosis for diabetic foot and pressure ulcer problems.

BRIEF SUMMARY

According to one aspect, a force sensor includes a polymeric substrate that includes a cavity with a tilt plane, at least two metal piezoresistors on the tilt plane, and a contact pad in electrical contact with the metal piezoresistors.

According to another aspect, a method of making a force sensor includes depositing a first layer of metal on a polymeric substrate to form a first set of metal piezoresistors, and bonding a contact pad on the first layer of metal. The polymeric substrate includes a cavity with a tilt plane, and the first layer of metal is deposited on at least a portion of the tilt plane.

BRIEF DESCRIPTION OF THE DRAWINGS

FIG. 3-(2) depicts a cross-sectional view of the second step of a fabrication process of the force sensor of FIG. 1.

FIG. 3-(3) depicts a cross-sectional view of the third step of a fabrication process of the force sensor of FIG. 1.

FIG. 3-(4) depicts a cross-sectional view of the fourth step of a fabrication process of the force sensor of FIG. 1.

FIG. 3-(5) depicts a cross-sectional view of the fifth step of a fabrication process of the force sensor of FIG. 1.

FIG. 3-(6) depicts a cross-sectional view of the sixth step of a fabrication process of the force sensor of FIG. 1.

FIG. 4-(2) depicts a cross-sectional view of the second step of a droplet sealing technique for making a polymeric substrate.

FIG. 4-(3) depicts a cross-sectional view of the third step of a droplet sealing technique for making a polymeric substrate.

FIG. 4-(4) depicts a cross-sectional view of the fourth step of a droplet sealing technique for making a polymeric substrate.

FIG. 4-(5) depicts a cross-sectional view of the fifth step of a droplet sealing technique for making a polymeric substrate.

FIG. 4-(6) depicts a cross-sectional view of the sixth step of a droplet sealing technique for making a polymeric substrate.

FIG. 6-(2) depicts a cross-sectional view of one of the corners of the second step of a fabrication process of the force sensor of FIG. 5A.

FIG. 6-(3) depicts a cross-sectional view of one of the corners of the third step of a fabrication process of the force sensor of FIG. 5A.

FIG. 6-(4) depicts a cross-sectional view of one of the corners after the third step of a fabrication process of the force sensor of FIG. 5A.

FIG. 6-(5) depicts a cross-sectional view of one of the corners of the fourth step of a fabrication process of the force sensor of FIG. 5A.

FIG. 6-(6) depicts a cross-sectional view of one of the corners of the fifth step of a fabrication process of the force sensor of FIG. 5A.

DETAILED DESCRIPTION

Reference will now be made in detail to a particular embodiment of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below, and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims. In addition, improvements and modifications which may become apparent to persons of ordinary skill in the art after reading this disclosure, the drawings, and the appended claims are deemed within the spirit and scope of the present invention.

Figure 1:
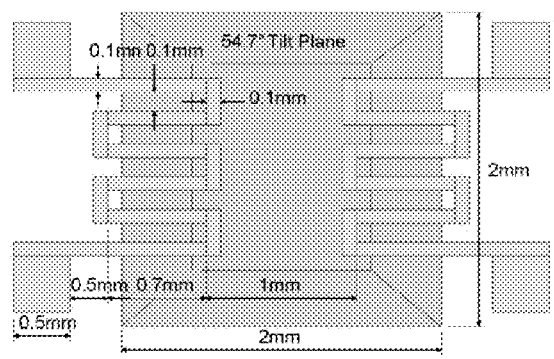
FIG. 1 depicts a top view of an embodiment of a one-axis force sensor.

A force sensor may include a polymeric substrate that includes a cavity with a tilt plane, at least two metal piezoresistors on the tilt plane, and a contact pad connected to the metal piezoresistors. The tilt plane may include an angle to a measured interface of from 15° to 75°. In one example, the tilt plane includes a 54.7° angle to the measured interface. A measured interface is a surface of the force sensor at which an external force is applied. A force sensor may include two piezoresistors aligned in mirror-image directions on the tilt planes, as depicted in FIG. 1. An interfacial shear and normal force sensor can be used to measure interfacial shear and normal strain by positioning the sensor in the interface between adjacent mated bodies.

Figure 2:
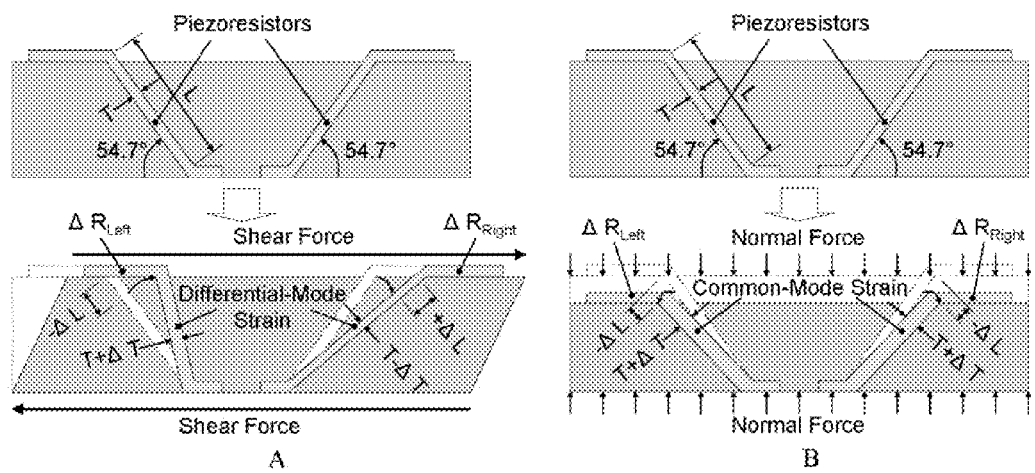
FIG. 2A depicts a cross-sectional view of the force sensor of FIG. 1 under a shear force.
FIG. 2B depicts a cross-sectional view of the force sensor of FIG. 1 under a normal force.

When a shear force is applied, the two piezoresistors may experience different directions of forces, as depicted in FIG. 2A. In particular, the force may compress the left piezoresistor to reduce the length by ΔL, and may stretch the right piezoresistor to increase the length by ΔL. Simultaneously, the thickness of the left piezoresistor may be increased by ΔT, and the thickness of the right piezoresistor may be decreased by ΔT.

When a normal force is applied, the two piezoresistors may also experience different directions of forces, as depicted in FIG. 2B. In particular, the force may compress the left and right piezoresistors to reduce the length by ΔL. Simultaneously, the thickness of the left and right piezoresistors may be increased by ΔT.

While not bound by theory, it is believed that the change of shape of the piezoresistor depends on the Poisson's ratio of the piezoresistive material, which is expressed as follows:

$$R = \rho \frac{L}{A}, \ A = W \cdot T, \ \Delta W = -W \cdot v \frac{\Delta L}{L}, \ \Delta T = -T \cdot v \frac{\Delta L}{L}$$

Where R=resistance, ρ=resistivity, L=length of the piezoresistor, W=width of the piezoresistor, T=thickness of the piezoresistor, v=Poisson's ratio.

The force may be measured with a strain-induced resistance change that depends on the gauge factor (GF) when a metallic piezoresistive material is employed. By measuring $\Delta R_{Right} - \Delta R_{Left}$, the common-mode (normal), strain-induced resistance change can be cancelled. This can allow the calculation of the pure shear force by subtracting the offset from the compressive force, which usually accompanies the shear force at the measured interface. Similarly, by measuring $\Delta R_{Right} + \Delta R_{Left}$, the differential-mode (shear), strain-induced resistance change can be cancelled, allowing a determination of the normal force.

Figure 3:
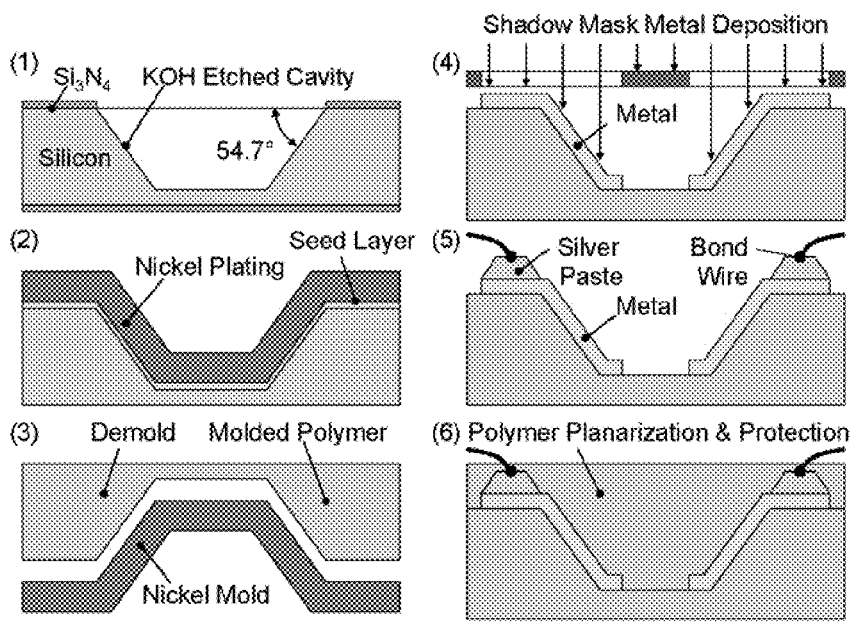
FIG. 3-(1) depicts a cross-sectional view of the first step of a fabrication process of the force sensor of FIG. 1.

An example of a method of making a one-axis force sensor is depicted in FIGS. 3-(1) to 3-(6). The first step includes providing a cavity mold with a tilt plane, as depicted in FIG. 3-(1). For example, a silicon wafer of (100) crystal orientation may be subjected to etching with potassium hydroxide (KOH). The anisotropic etching has a good etch stop on the (111) crystal plane of the silicon, with a much slower etch rate that is approximately 100 times slower than that of the (100) plane. A silicon nitride layer may serve as a hard mask for the KOH etching. The tilt plane may have an angle of from 15° to 75°. In one example, the title plane has an angle of 54.7°, corresponding to the difference in geometry of the (111) and (100) crystal planes. The etched cavity may have an inverted pyramid shape. The shape and geometry of the cavity may depend on the mold material and/or on the reagents and processes used for the etching.

The second step includes electroplating nickel on the cavity mold to form a negative nickel mold, as depicted in FIG. 3-(2). Other examples of the mold material include copper, brass, chromium, aluminum, iron, tin, zinc, indium, iridium, lead, arsenic, cadmium, cobalt, tellurium, tungsten, titanium, silver, gold, palladium, platinum, rhodium, silicon, and mixtures thereof. Other mold materials known to one of ordinary skilled in the art may also be used. A thin layer of sputtered gold may serve as a seed layer, and the nickel mold may be separated from the cavity mold by KOH etching.

The third step includes molding a polymer from the nickel mold to form a polymeric substrate that includes a cavity with a tilt plane, as depicted in FIG. 3-(3). The polymeric substrate may include a pyramid-shaped cavity with a 54.7° tilt plane, matching that of the cavity mold. However, a pyramid-shaped cavity with a tilt plane angle between 15° to 75° may also be used. The polymeric substrate may include polydimethysiloxane (PDMS), polyimide, and combinations thereof. The polymeric substrate may also include silicone or silicone-based materials (e.g. PDMS), rubber or rubber-based materials (e.g. latex, vinyl, nitrile), polymer or polymer-based materials (e.g. PMMA, acrylic, Bakelite, neoprene, nylon, PVC (polyvinyl chloride), polystyrene, polyacrylonitrile and PVB (polyvinyl butyral)), and epoxy-based materials (e.g. SU-8). The polymeric substrate may further include other materials known to one of ordinary skilled in the art to provide proper stiffness for the substrate.

Thus, the first three steps of this example together provide a polymeric substrate that includes a cavity with a tilt plane. In this example, the angle of the tilt plane of a cavity is determined by the shape of a corresponding inverted cavity of the master mold. Preferably, the tilt plane has an angle to a measured interface of from 15° to 75°.

The fourth step includes depositing a layer of metal on the tilt plane to form metal piezoresistors, as depicted in FIG. 3-(4). Metal may be deposited by shadow masking to block unwanted deposition from thermal evaporation or sputtering, while allowing deposition through the patterned openings. The metal may include copper, brass, chromium, aluminum, iron, tin, zinc, indium, iridium, lead, arsenic, cadmium, cobalt, tellurium, tungsten, titanium, silver, gold, palladium, platinum, rhodium, silicon, and mixtures thereof.

The deposited metal may be patterned on the substrate, including on the tilt planes. The metal deposition may include shadow masking, which may enable metal patterns to be formed on the tilt plane like a shadow. For example, two serpentine strain gauges may be laid on the tilt planes symmetrically, with opposite tilted angles. The serpentine design may increase the resistance of the metal piezoresistor to reduce the self-heating effect from joule heating when applying an electrical current.

The fifth step includes bonding a contact pad on the layer of metal, as depicted in FIG. 3-(5). The contact pad may be added after the shadow mask is removed, and may be used to make electrical connections. The contact pad may bond two wires to the metal layer with silver paste. For example, four contact pads may be included to make connections to the biasing current or voltage for measuring the resistance changes.

The sixth step includes filing the cavity with a layer of protective material, as depicted in FIG. 3-(6). The protective material may cover and flatten the cavity, and may also shield the metal piezoresistors and the contact pads. Examples of applicable materials include polydimethysiloxane (PDMS), polyimide, and combinations thereof. Other examples include silicone or silicone-based materials (e.g. PDMS), rubber or rubber-based materials (e.g. latex, vinyl, nitrile), polymer or polymer-based materials (e.g. PMMA, acrylic, Bakelite, neoprene, nylon, PVC (polyvinyl chloride), polystyrene, polyacrylonitrile and PVB (polyvinyl butyral)), and epoxy-based materials (e.g. SU-8). Other materials known to one of ordinary skilled in the art may also be used.

A polymeric substrate including a cavity with a tilt plane may be formed by other methods known to those skilled in the art. For example, a polymer may be molded onto a master mold that includes at least one inverted cavity. Separation of the polymer and the mold can provide a polymeric substrate that includes at least one cavity that corresponds to the at least one inverted cavity of the master.

Figure 4:
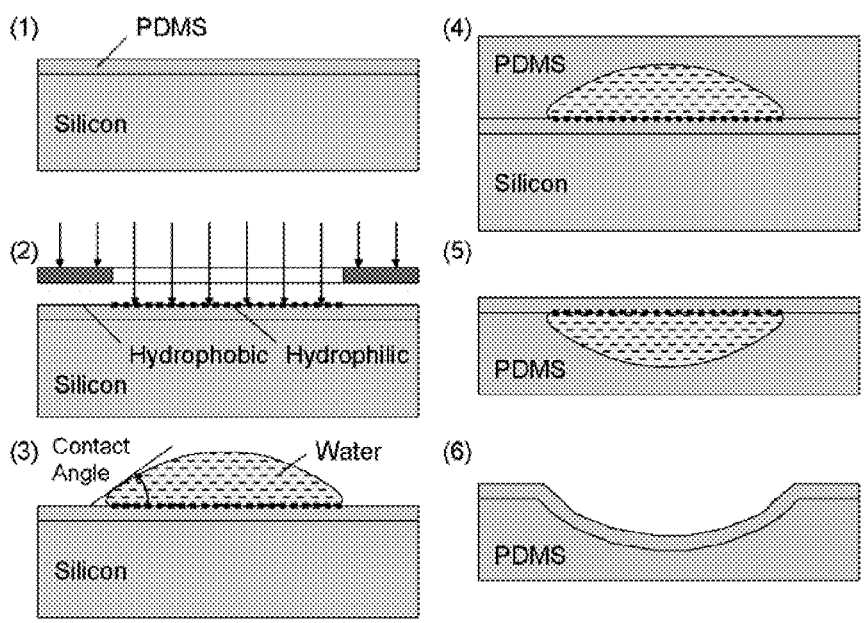
FIG. 4-(1) depicts a cross-sectional view of the first step of a droplet sealing technique for making a polymeric substrate.

Another method of preparing the polymeric substrate with the pyramid-shaped cavities is the PDMS water droplet sealing technique, as depicted in FIGS. 4-(1) to 4-(6). The first step includes spin-coating uncured PDMS solution onto a glass substrate and baking it to form a thin layer of PDMS on the substrate, as depicted in FIG. 4-(1). The second step includes using oxygen plasma treatment to selectively modify the surface of the PDMS-coated glass substrate through a shadow mask, as depicted in FIG. 4-(2). The exposed areas may become hydrophilic, whereas the unexposed areas may remain hydrophobic. The third step includes immersing the substrate into water and then taking it out. Water droplets may selectively occupy the hydrophilic areas, as depicted in FIG. 4-(3). The fourth step includes pouring uncured PDMS solution onto the substrate with patterned droplets. After curing, the patterned water droplets may be entirely sealed in the PDMS plate, as depicted in FIG. 4-(4). The fifth step includes peeling off the PDMS plate from the glass substrate, as depicted in FIG. 4-(5). The sixth step includes baking the PDMS plate to vaporize the sealed water droplets, due to the gas permeability of the PDMS material, and leaving the PDMS plate with pyramid-shaped cavities where the patterned droplets were once occupied, as depicted in FIG. 4-(6).

In this technique, therefore, controlling the contact angle of the water droplet from the hydrophobicity of the PDMS surface may give the pyramid-shaped cavities different tilt angles, for example, from 15° to 75°. The varying tilt angle may provide a range of sensitivity to the force sensor in normal or shear directions.

[2-D]

Figure 5:
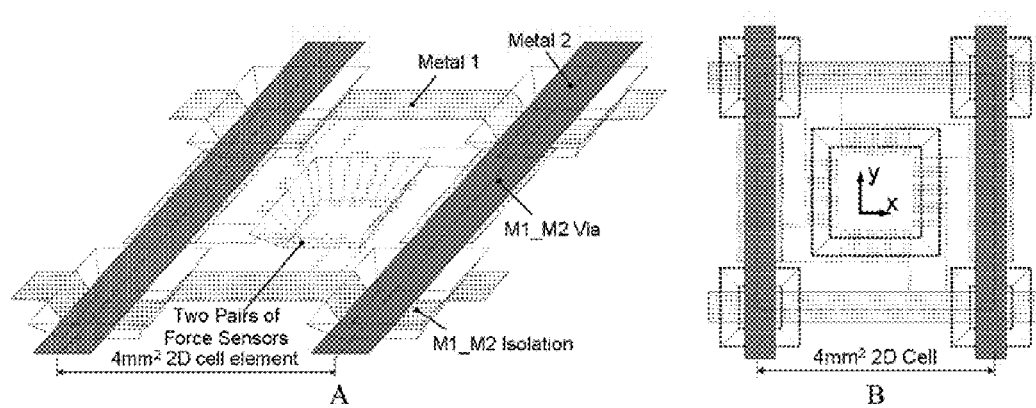
FIG. 5A depicts a perspective view of an embodiment of a 2-D force sensor.
FIG. 5B depicts a top view of the force sensor of FIG. 5A.

A two-dimensional (2-D) force sensor array may include multiple piezoelectric sensors, as depicted in FIGS. 5A and 5B. Each piezoelectric sensor may include two pairs of piezoresistors, allowing measurement of shear force for two perpendicular axes, and also allowing measurement of normal force. In one example, each pair may be electrically connected to a separate pair of electrodes.

To fabricate a 2-D force sensor array, a second layer of metal (Metal 2) may be deposited to provide vias for electrical connection to a first metal layer (Metal 1). A cross bridge may also be deposited to bypass Metal 1. A method of making a 2-D force sensor array is depicted in FIGS. 6-(1) to 6-(6).

Figure 6:
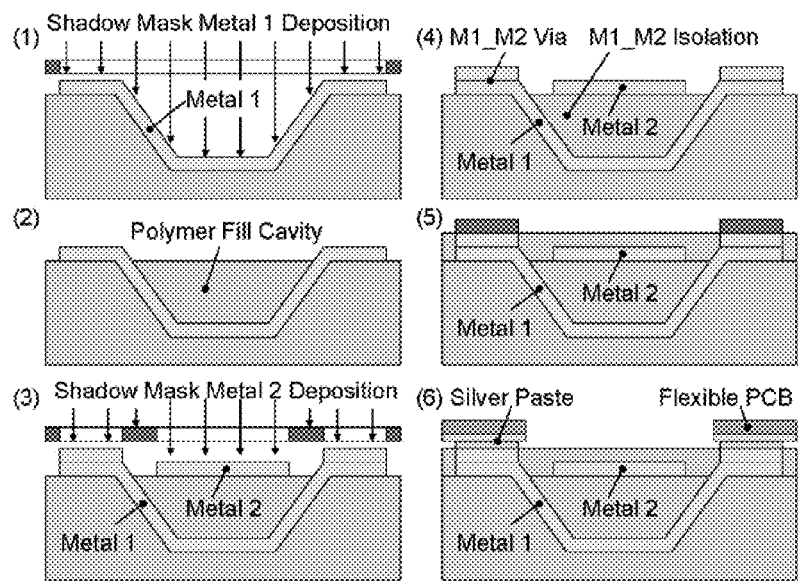
FIG. 6-(1) depicts a cross-sectional view of one of the corners of the first step of a fabrication process of the force sensor of FIG. 5A.

The first step includes providing a polymeric substrate that includes a cavity with a tilt plane, and depositing a first layer of metal on the tilt plane to form metal piezoresistors, as depicted in FIG. 6-(1). The polymeric substrate may be fabricated in the same way as described above.

The polymeric substrate may include a pyramid-shaped cavity with a 54.7° tilt plane. However, a pyramid-shaped cavity with a tilt plane angle between 15° to 75° may also be used. The polymer may include polydimethysiloxane (PDMS), polyimide, and combinations thereof. The polymeric substrate may also include silicone or silicone-based materials (e.g. PDMS), rubber or rubber-based materials (e.g. latex, vinyl, nitrile), polymer or polymer-based materials (e.g. PMMA, acrylic, Bakelite, neoprene, nylon, PVC (polyvinyl chloride), polystyrene, polyacrylonitrile and PVB (polyvinyl butyral)), and epoxy-based materials (e.g. SU-8). The polymeric substrate may further include other materials known to one of ordinary skilled in the art to provide proper stiffness for the substrate.

Metal may be deposited on the cavities by shadow masking to block unwanted deposition from thermal evaporation or sputtering, while allowing deposition through the patterned openings. The deposited metal may be patterned on the substrate, including on the tilt planes. The metal may include copper, brass, chromium, aluminum, iron, tin, zinc, indium, iridium, lead, arsenic, cadmium, cobalt, tellurium, tungsten, titanium, silver, gold, palladium, platinum, rhodium, silicon, and mixtures thereof.

The second step includes coating a layer of material to fill the cavity of the polymeric substrate, as depicted in FIG. 6-(2). Examples of applicable materials include polydimethysiloxane (PDMS), polyimide, and combinations thereof. Other examples include silicone or silicone-based materials (e.g. PDMS), rubber or rubber-based materials (e.g. latex, vinyl, nitrile), polymer of polymer-based materials (e.g. PMMA, acrylic, Bakelite, neoprene, nylon, PVC (polyvinyl chloride), polystyrene, polyacrylonitrile and PVB (polyvinyl butyral)), and epoxy-based materials (e.g. SU-8). A blade may be used to remove excess material that may extend out of the cavity. After curing, any residue on the first layer of metal may be cleaned with oxygen plasma.

The third step includes depositing a second layer of metal on the polymeric substrate, as depicted in FIG. 6-(3). Metal may be deposited on the cavities by shadow masking to block unwanted deposition from thermal evaporation or sputtering, while allowing deposition through the patterned openings. The metal may include copper, brass, chromium, aluminum, iron, tin, zinc, indium, iridium, lead, arsenic, cadmium, cobalt, tellurium, tungsten, titanium, silver, gold, palladium, platinum, rhodium, silicon, and mixtures thereof. The coated layer of material may provide isolation for the second metal layer from the first metal layer. The third step may establish a connection section (M1_M2 Via) to the first and second metal layers, and an isolation section (M1_M2 Isolation) between the first and second metal layers, as depicted in FIG. 6-(4).

The fourth step includes applying a protective layer of material and bonding a contact pad to the second layer of metal, as depicted in FIG. 6-(5). Examples of applicable materials include silicone or silicone-based materials (e.g. PDMS), rubber or rubber-based materials (e.g. latex, vinyl, nitrile), polymer of polymer-based materials (e.g. PMMA, acrylic, Bakelite, neoprene, nylon, PVC (polyvinyl chloride), polystyrene, polyacrylonitrile and PVB (polyvinyl butyral)), and epoxy-based materials (e.g. SU-8). The contact pad may be taped to allow contact to a flexible printed circuit board (PCB).

The fifth step includes attaching the contact pad to a flexible printed circuit board, as depicted in FIG. 6-(6). The pad area may be attached using silver paste.

[Calibration]

The force sensor may be calibrated to find its GF at different temperatures. To calibrate the force sensor, the sensor may be attached either to a vertical or to a horizontal stage, with a covering plate to sandwich the sensor and to apply either shear or normal force. The force may be applied with a set of standard weights. The resistance change of the force sensor may be measured with a Wheatstone bridge circuit by applying a constant bias voltage $V_B$. For example, for shear force sensor calibration, a differential-mode bridge Wheatstone configuration may be used to measure the resistance change, as depicted in FIG. 7A. For normal force sensor calibration, a common-mode Wheatstone bridge configuration may be used to measure the resistance change, as depicted in FIG. 7B. A calibration curve of resistance-versus-force (R-vs-F) may be plotted as a characterization of the force sensor. The linearity of the curve may be studied based on different designs of the force sensor.

The temperature coefficients of sensitivity (TCS) may be measured by placing the force sensor in a convection oven that can provide an elevated temperature to the overall setup without thermal gradient. Calibration curves for force sensing may be measured in a range of temperature, e.g., from 25° C. to 80° C. for each 5° C. elevation. This may generate a check table for the constants of the calibration curves. The force reading may be interpolated from these curves within the calibrated temperature range.

[Application]

The 2-D force sensor array may be used in pressure-mapping applications, including shoes fitting, seats and wheelchair seat designs, bed mattresses, dental occlusal analyses, tire track analyses, and prosthetic analyses.

In one example, the 2-D force sensor may be used in analysis of diabetic foot and/or in ergonomic studies on footwear. Pressure points on the foot, which may cause pressure ulcers of diabetic foot, may be displayed on a pressure-mapping image. In addition to the pressure generated by normal force, shear force is another key factor that may cause pressure ulcers. By using the force sensor array, both shear and normal force generated that pressure mapping images may be displayed separately, for an advanced analysis to improve footwear that can reduce localized pressure points. Consequently, a 2-D force sensor array may help to diagnose possible pressure ulcer locations in the foot for proper treatment.

EXAMPLES

Example 1

An Array of Force Sensors

Figure 7:
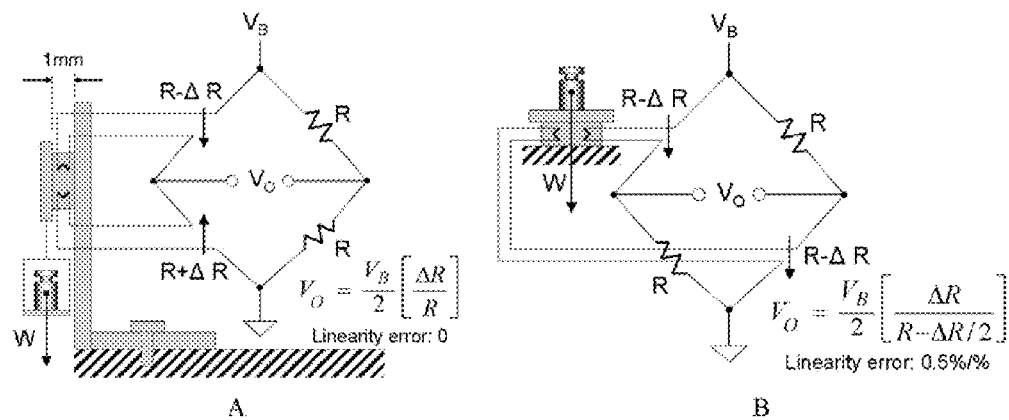
FIG. 7A depicts the shear force calibration of a force sensor using a Wheatstone bridge circuit to measure the resistance change.
FIG. 7B depicts the normal force calibration of a force sensor using a Wheatstone bridge circuit to measure the resistance change.
Figure 8:
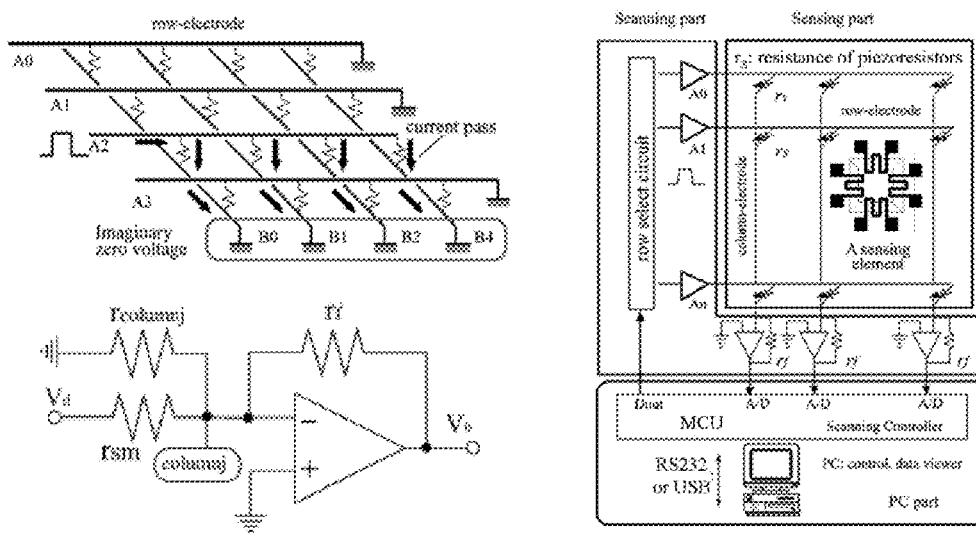
FIG. 8 depicts a zero potential scanning method as used in an array of force sensors.

A 16×16 2D array of force sensors was built for pressure mapping applications. A zero-potential scanning method was used to address individual elements that were on the intersections of row and column electrodes, as depicted in FIG. 7.

A zero-potential scanning method was based on turning off the unspecified row and column electrodes to have current only flow through the specified row to column electrical path, which eliminated cross-talk paths. The row electrodes were turned off with multiplexed switches, and the column electrodes were turned off with virtual ground from the amplifier. Each row-column cross had a piezoresistor connected for scanning. The scanned analog data was amplified, sent to an analog-to-digital (A/D) converter, saved in a microcontroller unit (MCU), and sent to a computer by recommended standard 232 (RS-232) or universal serial bus (USB). Software processed the data to show the pressure-mapping image of shear and normal force intensity with a color gradient.

Each pyramid-shaped cavity had two pairs of piezoresistors, allowing measurement of shear forces from two axes, which occupied four row-to-column crosses, as depicted in FIGS. 5A and 5B. Each unit cell contained four row-to-column intersections to address two pairs of force sensors with M1_M2 Via for connection and M1_M2 Isolation to cross the electrodes. Two metal layers were used to make M1 across M2 without touching, as depicted in FIG. 5A. A top view of the 4 mm$^2$ 2-D cell element is depicted in FIG. 5B.

Two pairs of one-axis sensors were aligned orthogonally in the x and y directions to sense both x- and y-components of the shear forces, while normal force was sensed in the z direction, perpendicular to the x-y plane. The pairs of one-axis sensors were the building blocks of the 2-D array. The pitches of the rows and columns were 4 mm, and were populated on a 4-inch wafer to create a 16×16 2-D array that had 256 piezoresistors, or 64 two-axis force sensor elements, with a 64×64 mm$^2$ area.

Example 2

Shadow Masking Technique

Figure 9:
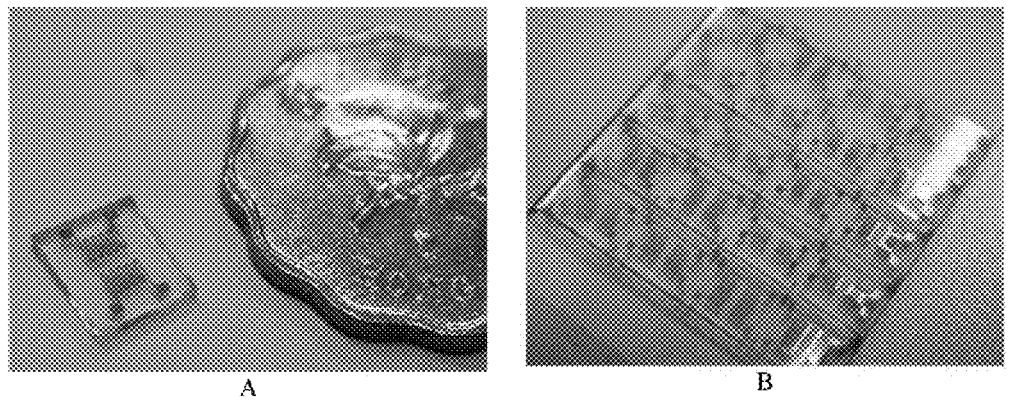
FIG. 9A depicts a pair of piezoresistors patterned on a piece of PDMS film.
FIG. 9B depicts various designs of piezoresistor pairs deposited on a PDMS film.

A shadow mask was made by wet etching of a stainless steel film with a thickness of 50 µm and a line width of 100 µm. A thin layer of PDMS film was made by coating the Dow Corning Sylgard 184 PDMS pre-polymer and its curing agent mixture on a glass substrate, and then curing at an elevated temperature of 70° C. in a convection oven. The cured PDMS film was subsequently covered with the shadow mask for sputtering with a thin layer of gold around 20 nm. A pair of piezoresistors was patterned on a piece of PDMS film, as depicted in FIG. 9A, where a 20-cent Hong Kong coin was used as a size reference. Various designs of piezoresistor pairs were deposited on the PDMS film, as depicted in FIG. 9B, which shows a 2-D force sensor array.

While the examples of the force sensor have been described, it should be understood that the composition not so limited and modifications may be made. The scope of the force sensor is defined by the appended claims, and all devices that come within the meaning of the claims, either literally or by equivalence, are intended to be embraced therein.

REFERENCES

U.S. Pat. No. 6,955,094 B1
U.S. Pat. No. 6,912,914 B2
U.S. Pat. No. 6,877,385 B2
U.S. Pat. No. 6,825,539 B2
U.S. Pat. No. 6,823,744 B2
U.S. Pat. No. 6,776,049 B2
U.S. Pat. No. 6,444,487 B1
U.S. Pat. No. 6,341,532 B1
U.S. Pat. No. 6,155,120
U.S. Pat. No. 6,071,819
U.S. Pat. No. 5,571,973
U.S. Pat. No. 5,490,427
U.S. Pat. No. 5,313,840
U.S. Pat. No. 4,155,265
US RE37,065 E

What is claimed is:

1. A force sensor, comprising:
    a polymeric substrate with a thickness comprising a cavity with a tilt plane at an angle to a measured interface;
    at least two metal piezoresistors on said tilt plane; and
    a contact pad in electrical contact with said metal piezoresistors; wherein said polymeric substrate and piezoresistors are flexible or deformable, permitting a change in said thickness and in said angle during operation of the force sensor; and wherein said cavity is pyramid-shaped and is filled with a protective material.

2. The force sensor of claim 1, wherein said angle is from 15° to 75°.

3. The force sensor of claim 1, wherein said angle is 54.7°.

4. The force sensor of claim 1, wherein said polymeric substrate comprises polydimethysiloxane, polyimide, latex, vinyl, nitrile, poly(methyl methacrylate), acrylic, Bakelite, neoprene, nylon, polyvinyl chloride, polystyrene, polyacrylonitrile, polyvinyl butyral, epoxy-based materials, or mixtures thereof.

5. The force sensor of claim 1, wherein said metal piezoresistors independently comprise copper, brass, chromium, aluminum, iron, tin, zinc, indium, iridium, lead, arsenic, cadmium, cobalt, tellurium, tungsten, titanium, silver, gold, palladium, platinum, rhodium, silicon, or mixtures thereof.

6. The force sensor of claim 1, wherein at least one of said metal piezoresistors comprises a serpentine strain gauge.

7. The force sensor of claim 1, furthering comprising a layer of protective material on at least a portion of said metal piezoresistors.

8. The force sensor of claim 7, wherein said protective material comprises polydimethysiloxane, polyimide, latex, vinyl, nitrile, poly(methyl methacrylate), acrylic, Bakelite, neoprene, nylon, polyvinyl chloride, polystyrene, polyacrylonitrile, polyvinyl butyral, epoxy-based materials, or mixtures thereof.

9. A pressure-mapping device, comprising at least two said force sensor of claim 1, wherein each force sensor is electrically connected to a separate pair of electrodes.

10. The pressure-making device of claim 9, wherein said device is selected from the group consisting of a diabetic foot sensor, a shoe-fitting sensor, a seat sensor, a wheelchair sensor, a bed mattress sensor, a dental occlusal analyzer, a tire track analyzer, and a prosthetic analyzer.

11. A method of determining a force with the sensor of claim 1, comprising:
measuring a difference in the change of resistance between said metal piezoresistors, and determining a shear force from said difference.

12. A method of determining a force with the sensor of claim 1, comprising:
measuring a sum of the change of resistance of said metal piezoresistors, and
determining a normal force from said sum.

13. A method of making a force sensor, comprising:
depositing a first layer of metal on a polymeric substrate to form a first set of metal piezoresistors;
bonding a contact pad on said first layer of metal,
wherein said polymeric substrate comprises a cavity with a tilt plane at an angle to a measured interface, and said first layer of metal is deposited on at least a portion of said tilt plane and said polymeric substrate is flexible or deformable, permitting a change of said angle of said tilt plane during operation of the force sensor; and
filling said cavity with a layer of protective material.

14. The method of claim 13, wherein said tilt plane comprises an angle to a measured interface of from 15° to 75°.

15. The method of claim 13, wherein said tilt plane comprises a 54.7° angle to a measured interface.

16. The method of claim 13, wherein said depositing comprises shadow masking.

17. The method of claim 13, further comprising forming said polymeric substrate from a negative mold.

18. The method of claim 17, wherein said negative mold comprises nickel electroplated on a cavity mold.

19. The method of claim 18, wherein said cavity mold comprises a seed layer.

20. The method of claim 18, wherein said cavity mold comprises silicon etched with potassium hydroxide.

21. The method of claim 13, wherein said filling is performed prior to bonding said contact pad on said first layer of metal.

22. The method of claim 21, further comprising depositing a second layer of metal on said tilt plane to form a second set of metal piezoresistors.

23. The method of claim 22, wherein said depositing comprises shadow masking.

24. The method of claim 22, further comprising establishing a connection section between said first and second metal layers, and establishing an isolation section between said first and second metal layers.

25. The method of claim 24, further comprising coating a layer of protective material, and bonding another contact pad on said second layer of metal.

26. The method of claim 25, further comprising attaching said contact pads to a flexible printed circuit board.

* * * * *